United States Patent
Rehe

(10) Patent No.: US 10,353,192 B2
(45) Date of Patent: Jul. 16, 2019

(54) ROD LENS SYSTEM FOR AN ENDOSCOPE AND ENDOSCOPE HAVING SUCH A ROD LENS SYSTEM

(71) Applicant: Henke-Sass, Wolf GmbH, Tuttlingen (DE)

(72) Inventor: Oliver Rehe, Wurmlingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 179 days.

(21) Appl. No.: 15/350,035

(22) Filed: Nov. 12, 2016

(65) Prior Publication Data

US 2017/0139197 A1 May 18, 2017

(30) Foreign Application Priority Data

Nov. 13, 2015 (DE) .......... 10 2015 119 622

(51) Int. Cl.
| | | |
|---|---|---|
| *A61B 1/002* | (2006.01) | |
| *G02B 13/00* | (2006.01) | |
| *G02B 13/18* | (2006.01) | |
| *G02B 23/24* | (2006.01) | |
| *G02B 27/00* | (2006.01) | |

(52) U.S. Cl.
CPC ............ *G02B 23/243* (2013.01); *A61B 1/002* (2013.01); *G02B 13/0095* (2013.01); *G02B 13/18* (2013.01); *G02B 23/2446* (2013.01); *G02B 27/0025* (2013.01)

(58) Field of Classification Search
CPC ........ G02B 23/24–2453; G02B 13/002; G02B 13/0095; G02B 13/18; G02B 27/0025; A61B 1/00; A61B 1/002; A61B 1/055
See application file for complete search history.

(56) References Cited

U.S. PATENT DOCUMENTS

| | | |
|---|---|---|
| 5,632,718 A | 5/1997 | Igarashi et al. |
| 6,088,157 A | 7/2000 | Mazurkewitz |
| 2008/0231949 A1 | 9/2008 | Mori |
| 2008/0273247 A1 | 11/2008 | Kazakevich |
| 2013/0194667 A1 | 8/2013 | Inoue |
| 2015/0256721 A1 | 9/2015 | Moore |

*Primary Examiner* — Stephone B Allen
*Assistant Examiner* — Adam W Booher
(74) *Attorney, Agent, or Firm* — Skaaar Ulbrich Macari, P.A.

(57) ABSTRACT

A rod lens system for an endoscope is provided, in which the rod lens system has at least one reversal stage, in order to image an intermediate image lying in a distal intermediate image plane into a proximal intermediate image plane, wherein each reversal stage has at least one rod lens and images an intermediate image into a next intermediate image plane, wherein the rod lens system is formed as an asymmetrical rod lens system and at least one of the reversal stages is formed as an asymmetrical reversal stage.

17 Claims, 1 Drawing Sheet

ROD LENS SYSTEM FOR AN ENDOSCOPE AND ENDOSCOPE HAVING SUCH A ROD LENS SYSTEM

PRIORITY

This application claims the benefit of German Patent Application No. 102015119622.0, filed on Nov. 13, 2015, which is hereby incorporated herein by reference in its entirety.

FIELD

The present invention relates to a rod lens system for an endoscope, in which the rod lens system has at least one reversal stage, in order to image an intermediate image lying in a distal intermediate image plane into a proximal intermediate image plane, wherein each reversal stage has at least one rod lens and images an intermediate image into a next intermediate image plane. In addition it relates to an endoscope with such a rod lens system.

BACKGROUND

A rod lens system is used in endoscopes to image an intermediate image, lying in a distal intermediate image plane, of an object to be observed by means of the endoscope into a proximal intermediate image plane and thus to relay the intermediate image.

As a rule, such rod lens systems have repeating rod lenses in symmetrical reversal stages, in order to keep the costs of the overall system low. Identical rod lenses are installed in opposite directions. This leads to the problem that a longitudinal chromatic aberration caused by the rod lens system can only be corrected with difficulty.

SUMMARY

The disclosure includes a rod lens system for an endoscope which reduces the problems discussed herein and overcome them as fully as possible. Furthermore, an endoscope with such a rod lens system is disclosed.

The disclosure includes a rod lens system formed as an asymmetrical rod lens system, wherein at least one of the reversal stages is formed as an asymmetrical reversal stage. It is thereby possible to provide several glasses and geometries (radii and thicknesses) in the rod lenses, whereby a better correction of the longitudinal chromatic aberration is possible.

Several reversal stages arranged one behind the other can be provided.

Each reversal stage is preferably formed such that it images an intermediate image into a next intermediate image plane. If several reversal stages arranged one behind the other are provided, these are preferably arranged such that the next intermediate image plane of a reversal stage coincides with the intermediate image plane from which the subsequent reversal stage images an intermediate image into the next intermediate image plane of this subsequent reversal stage.

In particular, the reversal stage, or reversal stages, of the rod lens system is, or are, arranged such that the intermediate image plane from which the reversal stage lying closest to the distal intermediate image plane images the intermediate image into the next intermediate image plane coincides with the distal intermediate image plane. In addition, the next intermediate image plane of the reversal stage which lies closest to the proximal intermediate image plane can coincide with the proximal intermediate image plane.

Each reversal stage preferably projects or images the intermediate image into the next intermediate image plane reversed or upside down. However, a projection the right way up is also possible.

Two reversal stages of the rod lens system can be formed as asymmetrical reversal stages. In particular, all reversal stages can be formed as asymmetrical reversal stages.

Furthermore, a first reversal stage, which lies closest to the distal intermediate image plane, can have a magnification factor greater than 1. A second reversal stage, which lies closest to the first reversal stage, can have a magnification factor smaller than 1. In particular, the first and second reversal stages together can have a magnification factor of 1.

Furthermore, one of the reversal stages can have a curved boundary surface, facing one of the intermediate image planes, which is aspherically curved. The aspherical curvature can have a rotational symmetry. However, it is also possible for the aspherical curvature not to have a rotational symmetry and to be curved differently in the two principal sections.

Preferably, at least one rod lens of each reversal system has at least one curved (e.g. spherically or aspherically curved) material boundary surface.

The reversal stages of the rod lens system can each have at least two rod lenses, wherein each of the reversal stages has two different rod lens types. By a rod lens type is meant in particular that rod lenses of the same type are formed identically. They thus have the same materials, the same dimensions and the same curvatures of the material boundary surfaces. In the reversal systems they can be arranged in the same direction as or in opposite directions to each other.

The rod lens system can include three or more reversal stages, wherein all of the reversal stages comprise a first rod lens of a first type, at least two of the three or more reversal stages comprise a second rod lens of the second type and at least one of the reversal stages comprises a third rod lens of the third type. The rod lenses of the first, second, and third type are different. An excellent correction of the longitudinal chromatic aberration is thus possible.

Furthermore, at least one of the rod lenses can be constructed from at least two parts. In particular, it can be formed as a cemented component. Furthermore, it is possible for at least one of the rod lenses to be formed in one piece.

Two reversal stages can be arranged symmetrically to each other.

The rod lens system can be configured in particular for rigid endoscopes or endoscopes with a rigid endoscope shaft.

The rod lenses of the reversal systems can have a diameter in the range of from 1 to 6.5 mm and in particular in the range of from 1.7 to 5 mm. The length of a reversal stage can lie in the range of from 30 to 120 mm. In particular, a length in the range of from 40 to 80 mm or a length of 60 mm is preferred.

The number of reversal stages of the rod lens system can lie in the range of from one to eleven or two to eleven reversal stages. An odd number of reversal stages is preferred. In particular, one reversal stage, three, five, seven, nine and eleven reversal stages are thus possible. Naturally it is also possible to provide an even number of reversal stages.

The rod lens system can in particular have a magnification factor in the range of from 0.5 to 2. Greater or smaller values are likewise possible.

The rod lenses can be formed from different materials. In particular, an individual rod lens can even be formed from two different materials. Glass and plastic materials are preferred in particular. A good chromatic aberration correction is thus possible.

The rod lens system can be formed such that during projection the principal rays are divergent in the proximal intermediate image plane. This leads to a greater distance of the exit pupil along the optical axis of the rod lens system. Alternatively, it is possible for the principal rays to be convergent, which leads to a smaller distance of the exit pupil. A better adaptation to e.g. camera systems to be provided for capturing the intermediate image from the proximal intermediate image plane is thus possible.

The use of one or more aspherical material boundary surfaces in the rod lenses can be utilized in particular to reduce vignetting of the overall optical system and/or to reduce the aspherical aberration of the overall system. A reduced vignetting leads to a greater marginal brightness and a reduction of the aspherical aberration leads to a greater marginal sharpness.

With the disclosed rod lens system, the image field curvature can be corrected, which leads to an image shell which has a greater evenness, whereby a greater marginal sharpness during projection is achieved. In addition, astigmatism can be corrected, whereby in turn the marginal sharpness during projection can be improved.

The rod lenses of at least one reversal stage and/or the reversal stages preferably have a common optical axis.

Furthermore, an endoscope with a rod lens system as disclosed herein can include an objective lens which is arranged in front of the rod lens system. In particular, the objective lens is formed such that it images an object to be imaged into the distal intermediate image plane.

In addition, the endoscope can include an optics unit, such as e.g. an eyepiece, arranged after the rod lens system.

The endoscope can further include features known to a person skilled in the art which are necessary for the operation of the endoscope.

In particular, the endoscope can be formed as an endoscope with a rigid shaft in which the rod lens system according to the disclosure is arranged.

It is understood that the features named above and those yet to be explained below can be used not only in the stated combinations but also in other combinations or alone, without departing from the scope of the present invention.

Figure 1:
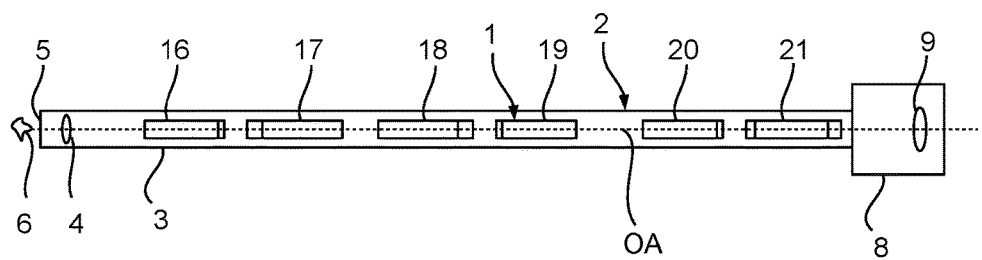
FIG. 1 is a schematic representation of a rod lens system according to the invention in an endoscope.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration rather than to limit the present invention.

In the embodiment shown in FIG. 1 the rod lens system 1 according to the invention is shown in a schematically represented endoscope 2, wherein the rod lens system 1 is arranged in a rigid shaft 3 of the endoscope 2.

Figure 2:
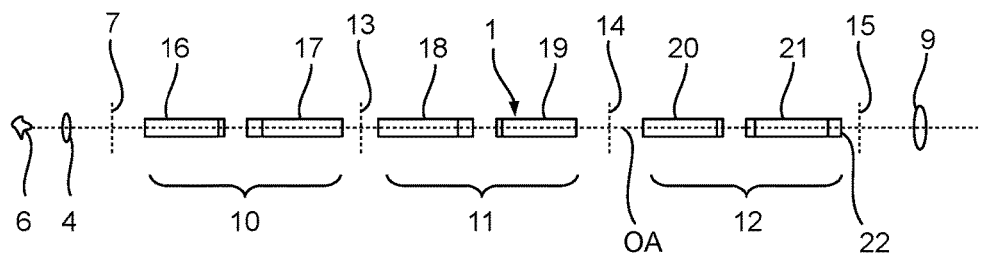
FIG. 2 is a schematic representation of an overall optical system of the endoscope of FIG. 1.

In the shaft 3, furthermore, a schematically represented objective lens 4 is arranged which images an object 6 located in front of the distal end 5 of the shaft 3 into a first intermediate image plane 7, which can also be called the distal intermediate image plane 7 (FIG. 2). Furthermore, the endoscope 2 comprises a main part 8 in which further optics can be arranged, such as e.g. the schematically represented eyepiece 9.

The rod lens system 1 according to the invention has a first, a second and a third reversal stage 10, 11, 12, which are arranged one behind the other and each project an intermediate image into a next intermediate image plane. The first reversal stage 10 thus projects the intermediate image lying in the first intermediate image plane 7 into a second intermediate image plane 13. The second reversal system 11 projects the intermediate image lying in the second intermediate image plane 13 into a third intermediate image plane 14. The third reversal system 12 projects the intermediate image from the third intermediate image plane 14 into a fourth intermediate image plane 15, which can also be called the proximal intermediate image plane 15. The three reversal systems 10-12 are thus arranged one behind the other such that an intermediate image lying in the distal intermediate image plane 7 is projected (via in each case the next intermediate image planes 13 and 14) into the proximal intermediate image plane 15. Since each reversal stage 10-12 during the projection of the intermediate image produces a reversed intermediate image and an odd number of reversal stages 10-12 are provided, the intermediate image of the object 6 lying in the distal intermediate image plane 7 is projected into the proximal intermediate image plane 15 as a reversed intermediate image. The rod lens system 1 therefore can also be called a reversal system 1.

The eyepiece 9 is arranged after the rod lens system 1, with the result that a user can perceive the intermediate image projected into the proximal intermediate image plane 15 by means of the eyepiece 9. Naturally it is also possible to provide, instead of the eyepiece 9, other optics in order e.g. to capture the intermediate image lying in the proximal intermediate image plane 15 by means of a camera (not shown) and to present it via a display system (not shown).

The rod lens system 1 is formed as an asymmetrical rod lens system 1. In addition, in the embodiment example described here all three reversal stages 10-12 are also each formed asymmetrically.

Due to the asymmetrical formation of the rod lens system 1, for example, the longitudinal chromatic aberration can be corrected better than in symmetrical rod lens systems.

Furthermore, the rod lens system 1 can be designed such that a desired image size in the proximal intermediate image plane 15 is achieved. Telecentry characteristics or the position of the exit pupil along the optical axis OA of the rod lens system 1 can also be adjusted.

Because the rod lens system 1 can be corrected better than the conventional rod lens systems, e.g. the outlay on correction for the objective lens 4 and/or the eyepiece 9 can prove to be smaller. Thus, in particular, the distortion of the entire imaging system is improved because of the asymmetrical rod lens system.

The asymmetrical formation of the reversal stages 10-12 is realized by providing in each case two rod lenses 16, 17; 18, 19 and 20, 21, which are different or not of the same type, per reversal stage 10-12. In particular, in the rod lens system described, three differently formed rod lenses are provided which can be called type A, type B and type C. The rod lenses of the same type are characterized by the fact that their optical parameters are the same. This means that they have the same materials, dimensions, curvature of boundary surfaces. Thus, rod lenses 16, 19 and 20 are of type A, wherein rod lenses 16 and 20 have the same orientation (thus are arranged in the same direction) and rod lens 19 is arranged rotated by 180° relative to rod lenses 16 and 20 (thus are arranged in opposite directions). Rod lenses 17 and 18 are of type B and are arranged rotated by 180° relative to each other. Rod lens 21 is of type C.

The rod lens system 1 thus has the following sequence of rod lenses: A-B-B-A-A-C.

The first reversal stage 10 has a magnification factor greater than 1 and the second reversal stage 11 has a magnification factor smaller than 1. The combination of the first and second reversal stages 10 and 11 together has a magnification factor or ratio of 1, with the result that the intermediate image lying in the first intermediate image plane 7 is projected into the third intermediate image plane 14 as a 1:1 projection. The first and second reversal stages 10, 11 are arranged symmetrically to each other (relative to the second intermediate image plane 13).

The third reversal stage 12 can have a magnification factor which lies, for example, in the range of 0.7-1.3.

The representations of the reversal stages 10-12 are purely schematic. In fact, the boundary surfaces of the individual rod lenses 16-21 are preferably curved. In the embodiment described here, rod lenses 16-20 are each formed in two parts, wherein the two parts are formed from different materials. Rod lens 21 is formed in three parts and can have two or even three different materials.

It is particularly preferred to form the boundary surface 22 facing the proximal intermediate image plane 15 as an aspherical surface. The aspherical surface can be rotationally symmetrical or also can have no rotational symmetry. In particular, it can have two different curvatures in the two principal sections.

Figure 3:
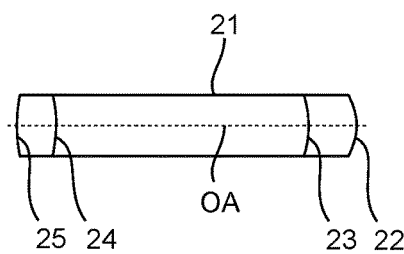
FIG. 3 is an enlarged view of rod lens of a third reversal system.

As can be seen from the enlarged schematic representation in FIG. 3, all boundary surfaces or material boundary surfaces 22, 23, 24 and 25 of rod lens 21 are formed curved.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. A rod lens system for an endoscope, comprising:
   at least one reversal stage configured to image an intermediate image lying in a distal intermediate image plane into a proximal intermediate image plane,
   wherein each reversal stage includes at least one rod lens and is configured to image an intermediate image into a next intermediate image plane,
   wherein the rod lens system comprises an asymmetrical rod lens system,
   wherein at least one of the reversal stages comprises an asymmetrical reversal stage, and
   wherein a first reversal stage, which lies closest to the distal intermediate image plane, has a magnification factor greater than 1.

2. The rod lens system according to claim 1, wherein several reversal stages are arranged one behind the other.

3. The rod lens system according to claim 1, wherein at least two reversal stages are configured as asymmetrical reversal stages.

4. The rod lens system according to claim 1, in which all reversal stages are formed as asymmetrical reversal stages.

5. The rod lens system according to claim 1, comprising at least three reversal stages, wherein all reversal stages comprise a first rod lens of a first type, at least two of the at least three reversal stages comprise a second rod lens of a second type and at lease one of the at least three reversal stages comprises a third rod lens of a third type.

6. The rod lens system according to claim 1, wherein a second reversal stage, which lies closest to the first reversal stage, has a magnification factor smaller than 1.

7. The Rod lens system according to claim 6, comprising at least three reversal stages, wherein all reversal stages comprise a first rod lens of a first type, at least two of the at least three reversal stages comprise a second rod lens of a second type and at lease one of the at least three reversal stages comprises a third rod lens of a third type.

8. The rod lens system according to claim 6, wherein the first and second reversal stages together have a magnification factor of 1.

9. The Rod lens system according to claim 8, comprising at least three reversal stages, wherein all reversal stages comprise a first rod lens of a first type, at least two of the at least three reversal stages comprise a second rod lens of a second type and at lease one of the at least three reversal stages comprises a third rod lens of a third type.

10. The rod lens system according to claim 8, wherein a third reversal stage has a magnification factor of 0.7-1.3.

11. The Rod lens system according to claim 10, comprising at least three reversal stages, wherein all reversal stages comprise a first rod lens of a first type, at least two of the at least three reversal stages comprise a second rod lens of a second type and at lease one of the at least three reversal stages comprises a third rod lens of a third type.

12. The rod lens system according to claim 1, wherein at least one of the reversal stages includes a curved boundary surface, facing one of the intermediate image planes, which is aspherically curved.

13. The rod lens system according to claim 1, wherein the reversal stages each include at least two rod lenses, wherein each of the reversal stages comprises at least two different rod lens types.

14. The rod lens system according to claim 1, wherein at least one of the rod lenses comprises at least two parts.

15. The rod lens system according to claim 1, wherein at least two reversal stages are arranged symmetrically to each other.

16. An endoscope, comprising:
a rod lens system the rod lens system including at least one reversal stage configured to image an intermediate image lying in a distal intermediate image plane into a proximal intermediate image plane,
wherein each reversal stage includes at least one rod lens and is configured to image an intermediate image into a next intermediate image plane,
wherein the rod lens system comprises an asymmetrical rod lens system,
wherein at least one of the reversal stages comprises an asymmetrical reversal stage, and
wherein the rod lens system comprises a first reversal stage, which lies closest to the distal intermediate image plane, that has a magnification factor greater than 1.

17. The endoscope of claim 16, wherein the rod lens system comprises at least three reversal stages, wherein all reversal stages comprise a first rod lens of a first type, at least two of the at least three reversal stages comprise a second rod lens of a second type and at lease one of the at least three reversal stages comprises a third rod lens of a third type.

* * * * *